(12) United States Patent
Keimer et al.

(10) Patent No.: US 8,231,829 B2
(45) Date of Patent: Jul. 31, 2012

(54) DEVICE FOR MANIPULATING AT LEAST ONE SPECIMEN SLIDE

(75) Inventors: Simon Keimer, Nussloch (DE); Juergen Tenhaef, Brombachtal (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 199 days.

(21) Appl. No.: 12/559,972

(22) Filed: Sep. 15, 2009

(65) Prior Publication Data

US 2010/0068095 A1 Mar. 18, 2010

(30) Foreign Application Priority Data

Sep. 17, 2008 (DE) .......................... 10 2008 047 575

(51) Int. Cl.
*G01N 1/28* (2006.01)

(52) U.S. Cl. ............ 422/65; 422/63; 422/500; 422/536; 435/288.3; 436/46

(58) Field of Classification Search .................. None
See application file for complete search history.

(56) References Cited

U.S. PATENT DOCUMENTS

| | | | |
|---|---|---|---|
| 5,305,650 A * | 4/1994 | Koike et al. ................ | 73/864.21 |
| 6,796,353 B2 | 9/2004 | Lang et al. | |
| 7,566,366 B2 | 7/2009 | Kiene | |
| 2004/0114227 A1* | 6/2004 | Henderson et al. ........... | 359/391 |
| 2005/0186114 A1 | 8/2005 | Reinhardt et al. | |
| 2007/0288124 A1* | 12/2007 | Nagata et al. ................ | 700/258 |
| 2012/0009101 A1* | 1/2012 | Berberich et al. ............ | 422/536 |

FOREIGN PATENT DOCUMENTS

| | | |
|---|---|---|
| DE | 10144048 A1 | 3/2003 |
| DE | 102005020426 A1 | 11/2006 |
| EP | 1803536 A1 | 8/2005 |
| GB | 2366376 A | 3/2002 |
| JP | 2001-9772 * | 1/2001 |

* cited by examiner

*Primary Examiner* — P. Kathryn Wright
(74) *Attorney, Agent, or Firm* — Leydig, Voit & Mayer, Ltd.

(57) ABSTRACT

A device for manipulating at least one specimen slide. The device includes a first sensor unit operable to sense a first rotation of a first component of the device about at least one first axis of a three-dimensional coordinate system. A second sensor unit is operable to sense a second rotation of a second component of the device about the at least one first axis of the coordinate system, the coordinate system being independent of a position of the first component and of a position of the second component. A positioning unit is operable to position the second component relative to the first component.

7 Claims, 6 Drawing Sheets

US 8,231,829 B2

DEVICE FOR MANIPULATING AT LEAST ONE SPECIMEN SLIDE

CROSS REFERENCE TO RELATED APPLICATIONS

Priority is claimed to German Patent Application No. DE 10 2008 047 575.0, filed Sep. 17, 2008, which is hereby incorporated by reference herein.

FIELD

The invention relates to a device for manipulating at least one specimen slide, in which, for reliable function, two components of the device are be arranged in a correct position relative to one another.

BACKGROUND

Especially in the context of devices for manipulating specimen slides that automatically carry out working steps when handling a specimen slide, it is often necessary for components of the respective device to be correctly oriented with respect to one another. Such components contact the specimen slide directly and/or contact the samples to be brought into contact with the specimen slide or further elements to be brought into contact with the specimen slide. For correct positioning of the specimen slide and/or of the sample or the further elements, the components of the device should be correctly oriented with respect to one another. Such devices for manipulating specimen slides include, in particular, a unit for automatically applying a biological sample onto a specimen slide, a unit for automatically cleaning a biological sample, a unit for automatically staining a biological sample arranged on the specimen slide, and/or a unit for automatically covering a biological specimen, arranged on the specimen slide, with a coverslipping agent and/or a coverslip.

DE 101 44 048 A1 describes an apparatus for manipulating specimen slides and coverslips. In this, a coverslip is picked up with the aid of a pickup unit guided via an actuation arm, and is placed onto a desired position on the specimen slide. Automatic apparatuses of this kind for the application of coverslips onto specimen slides are also referred to as "coverslippers." The coverslips serve in this context to cover a prepared specimen present on a specimen slide. A prepared specimen of this kind is preferably a biological sample, such as a histological section. The coverslips are thin, preferably having a thickness of approx. 0.17 mm, and are made available in a stack. In order to pick up a coverslip from the stack, the pickup unit must therefore be exactly positioned with respect to the stack in order to pick up the topmost coverslip of the stack. In the same fashion, upon placement of the coverslip onto the specimen slide, the coverslip or the pickup unit having the coverslip must be exactly positioned with respect to the specimen slide. If deviations occur during positioning of the coverslip and the pickup unit, the risk exists that the glass of the coverslip and/or of the specimen slide may break.

DE 10 2005 020 426 A1 describes a coverslipping machine for applying coverslipping agent and a coverslip onto a specimen slide. Here, in particular, the means for picking up and positioning the coverslip on the specimen slide must be oriented exactly with respect to a holder of the specimen slide so that exact positioning of the coverslip can be carried out, and furthermore in order to avoid damage to or destruction of the coverslip.

In coverslipping machines, it is usual to orient the basic device itself in three dimensions with the aid of auxiliary means for leveling a base frame of the basic device, and additionally to orient an actuation element positionable with respect to the base frame, or a holding element for the actuation element, relative to the base frame, so that these elements are likewise oriented exactly in three dimensions with reference to a horizontal plane. The actuation arm, or a mount for the actuation arm, is usually connected to the base frame, and auxiliary alignment means can be provided in order to orient the actuation arm relative to the base frame of the coverslipping machine.

Problems similar to those with the coverslipping machine also occur with other devices for manipulating specimen slides with which preferably automatic preparation of a sample for microscopic investigation is carried out.

SUMMARY

An aspect of the present invention is to provide a device for manipulating at least one specimen slide in which correct positioning of two components of the device relative to one another is possible in relatively simple fashion.

In an embodiment, the present invention provides a device for manipulating at least one specimen slide. The device includes a first sensor unit operable to sense a first rotation of a first component of the device about at least one first axis of a three-dimensional coordinate system. A second sensor unit is operable to sense a second rotation of a second component of the device about the at least one first axis of the coordinate system, the coordinate system being independent of a position of the first component and of a position of the second component. A positioning unit is operable to position the second component relative to the first component.

BRIEF DESCRIPTION OF THE DRAWINGS

Exemplary embodiments of the present invention are described in the following with reference to the drawings, in which.

DETAILED DESCRIPTION

Figure 1:
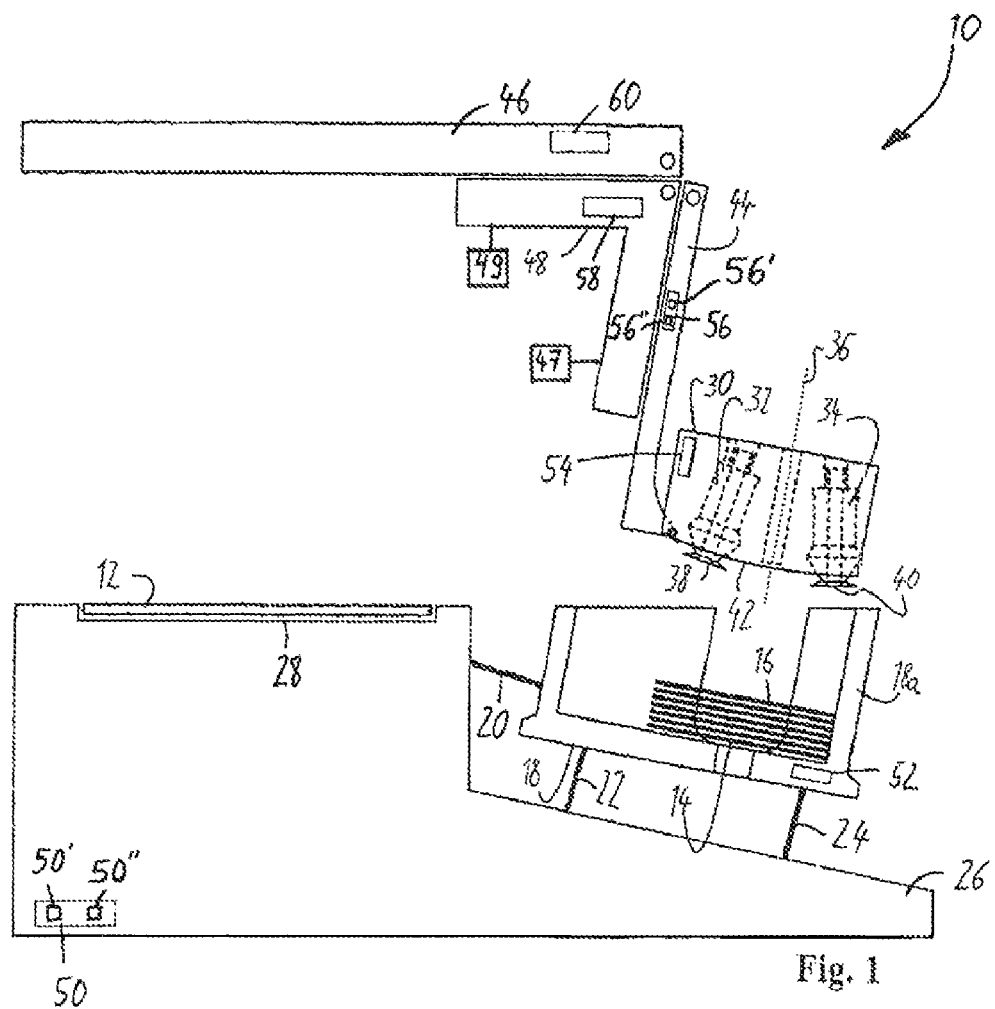
FIG. 1 is a side view of an arrangement of components of a device for covering specimen slides with a coverslip, in accordance with an embodiment of the invention, in a rest position.

By means of the sensor units, at least one respective rotation of a component of the device about a first axis of the coordinate system is ascertained. Based on the rotation thereby ascertained about an axis of a coordinate system that is independent of the position of the components of the device, a difference in the rotation of the components about said axis can also be ascertained, and from that difference a correction value is determined which is then taken into account by the positioning unit for positioning of the second component, or is used as an initial variable for positioning of the second component relative to the first component. Alternatively, the positioning unit can be actuated manually, the ascertained deviation or the ascertained correction value serving as an indication of the correction to be brought about by manual positioning. A correction value can be repeatedly determined and outputted in this context, in order to carry out stepwise positioning of the second component with respect to the first component into a desired relative rest position of the second component relative to the first component. The coordinate system that is independent of the position of the components of the device is also referred to as a three-dimensional coordinate system and can be, for example, a world coordinate system or a base coordinate system.

In one embodiment, the positioning unit may include at least one drive unit and at least one control unit. The control unit applies control to the drive unit in such a way that the drive unit positions the second component as a function of the rotation, sensed with the aid of the first sensor unit, of the first component about the first axis, and as a function of the second rotation, sensed with the aid of the second sensor unit, of the second component about the first axis, in such a way that during operation of the device, the first component selectably has a first target position or a second target position relative to the second component. The target position refers at least to the difference between the rotation of the first component about the first axis and the rotation of the second component about the first axis. In one embodiment, the drive unit may include at least one stepping motor and/or at least one linear motor.

In particular, the first component can include a base module of the device. The base module has a pickup unit for picking up at least one specimen slide and/or at least one cassette having multiple specimen slides. The specimen slide and/or specimen slides of the cassette have, as a result of pickup, a position relative to the base module that is defined by the base module. The second component encompasses an actuation element, movable relative to the base module, of the device. The actuation element is movable relative to the base module with the aid of a drive unit. With the aid of such an arrangement, the actuation element can be oriented and positioned correctly with respect to the base module so that the element can perform a desired movement with reference to the specimen slide. The actuation element can serve in particular to pick up the specimen slide or to apply samples, substances, and/or elements onto the specimen slide.

In one embodiment, the device has a third sensor unit that senses a rotation of a second actuation element, movable relative to the base module of the device about the at least one axis of the coordinate system. As a result, the relative rotation of the first actuation element and of the second actuation element with respect to one another can also be ascertained and, if necessary, corrected. In particular, a correction value can be determined that is taken into account in the context of a movement of the first and/or second actuation element.

Alternatively, the first component of the device can be a first actuation element, movable relative to a base module of the device with the aid of a drive unit. The second component can then be a second actuation element, movable relative to the base module of the device with the aid of a further drive unit relative to the base module and/or relative to the first component of the device. Alternatively, the second component can be connected immovably to the base module. What is achieved thereby is that the first actuation element and the second actuation element can be positioned in a target position with respect to one another. This can also occur independently of the positions of the components with respect to the base module of the device.

Additionally or alternatively to the drive unit, the positioning unit can have at least one aligning means at least for modifying the rest position of the first component in three dimensions and/or for modifying the rest position of the second component in three dimensions. Furthermore, additionally or alternatively, an aligning means can be provided for modifying the rest position of the first component relative to the second component. An aligning means of this kind can, in particular, be actuated manually in order to bring the components into a desired target position with respect to one another, and thereby to ensure smooth and correct functioning of the components during subsequent operation. An aligning means of this kind can be, for example, an adjusting screw with which the positions of the components relative to one another, or in three dimensions, can be modified.

It is additionally possible to ascertain, as an indication of the first rotation, the angle between a reference axis of the first component and a second axis of the coordinate system. The angle between a reference axis of the second component and the second axis of the coordinate system can furthermore be ascertained as an indication of the second rotation. By means of the angle with respect to the second axis of the coordinate system, it is easy to determine the difference angle between the first component and the second component with reference to the reference axis of the respective component, and to compare it with a target difference angle. As a function of the deviation of the ascertained difference angle from the target difference angle, a correction value can be calculated or a positioning action of at least one component can be authorized, which action causes the angular difference between the reference axes of the components to correspond to the target angular difference.

In some embodiments, the reference axis of the components can be projected into a plane in which the second and a third axis of the coordinate system extend, and which extends orthogonally to the first axis of the coordinate system. Alternatively, the reference axis can already extend in the plane. This can be ascertained in the same fashion for the second component. The angular deviations of the reference axes of the components with respect to the second axis of the coordinate system can thereby easily be determined. With the aid of the angle thus ascertained, it is also easy to ascertain an angular difference between the angles and to compare it with a target angular difference. Based on the deviation of the ascertained angular difference from the target angular difference, corresponding correction values for positioning at least one of the components can be determined, by means of which values the components are then arranged at the desired target angle with respect to one another.

The sensor units can each include at least one microelectromechanical system (MEMS). A microelectromechanical system of this kind may include a gyroscope and/or an acceleration sensor. Inclinometers, in particular, may be utilized. Using a gyroscope, it is easy to ascertain in simple fashion positional deviations with respect to two axes of a three-dimensional coordinate system, such as a world coordinate system or a base coordinate system. It is possible in particular, with the aid of the gyroscope, to ascertain rotations about the axes of the coordinate system that lie in a horizontal plane of the coordinate system. Deviations from a target position of the components, resulting from a rotation about said axes, can be detected and eliminated by way of a suitable arrangement of the sensor units on the components. Alternatively, a correction value can be calculated which is then taken into account in terms of the control and movement of at least one component.

In an embodiment, the first sensor unit can sense a first rotation of the first component about the first axis of the coordinate system, and a third rotation of the first component about a second axis of the coordinate system, and if the second sensor unit senses the second rotation of the second component about the first axis of the coordinate system and a fourth rotation of the second component about the second axis of the coordinate system.

In an embodiment, the rotation of the components about the X axis and the Y axis, which lie in one horizontal plane, is ascertained.

In addition, the first sensor unit can sense a fifth rotation of the first component about a third axis, for example the Z axis, of the coordinate system. The second sensor unit can then additionally sense a sixth rotation of the second component about a third axis of the coordinate system. The respective position of the component in three dimensions can thereby be determined, so that positional deviations in the positions of the components relative to one another can be ascertained in simple fashion by corresponding difference calculations and geometrical relationships.

For this purpose, each sensor unit can respectively include at least two sensor modules that then respectively sense the rotations of the components about two axes of the coordinate system.

The first sensor unit may be a constituent of the first component or is connected thereto. The second sensor unit may be a constituent of the second component or is connected thereto. The respective component of the device includes at least one subassembly of the device. As a result, the positions of subassemblies of the device with respect to one another can be ascertained in simple fashion and corrected if necessary. For correction, it is possible to calculate a correction value that is then taken into account when applying control to at least one drive unit for positioning a subassembly of the device.

FIG. 1 schematically depicts an apparatus 10 for the manipulation of at least one specimen slide 12 and of coverslips arranged in a stack 14. The upper coverslip of stack 14 is labeled with the reference character 16. Stack 14 is arranged in a magazine 18. Magazine 18 is connected via adjusting screws 20 to 24 to a base frame 26 of apparatus 10. The position of magazine 18, and thus of stack 14, relative to base frame 26 can be modified via adjusting screws 20 to 24.

Base frame 26 has a receiving region 28 for receiving at least one specimen slide 12. Specimen slide 12 may be removed automatically, with the aid of a further apparatus, from a specimen slide magazine and arranged in specimen receiving region 28 of base frame 26 for further manipulation. Apparatus 10 further includes a pickup unit 30 that, in the present exemplifying embodiment, includes two pickup elements 32, 34. Pickup elements 32, 34 can each be moved in the direction of their longitudinal axis relative to pickup unit 30, pickup elements 32, 34 being arranged in such a way that their longitudinal axes do not extend in parallel fashion and preferably enclose an acute angle between pickup elements 32, 34.

Pickup elements 32, 34 are arranged in mirror-symmetrical fashion with respect to a center axis 36 of pickup unit 30. Pickup elements 32, 34 each have, at their end facing toward stack 14, at least one suction element 38, 40 that, upon contact with upper coverslip 16 of stack 14, secures itself by suction by means of a negative pressure then applied at suction element 38, 40. After at least one suction element 38, 40 is secured by suction on coverslip 16, the pickup element 32, 34 comprising that suction element 38, 40 is additionally moved, by the applied negative pressure, along its respective longitudinal axis so that suction elements 38, 40 retract into pickup unit 30, i.e. are moved upward in FIG. 1, so that they then no longer, or only insignificantly, protrude out of the curved end face 42 of pickup unit 30. Coverslips 16 removed from stack 14 are bent as a result of the arrangement of pickup elements 32, 34 and of the curved end face 42 of pickup unit 30. Arranged between pickup elements 32, 34 and a base frame of pickup unit 30 is a bellows that, after the respective suction element 38, 40 is secured by suction on upper coverslip 16, is compressed by the negative pressure applied to the bellows. As a result of the compression of the bellows, the respective pickup unit 32, 34 is displaced in the direction of its longitudinal axis. Pickup unit 30 is connected via a linear stroke element 44 to an angle element 48 arranged displaceably on a transport arm 46. Pickup unit 30 is depicted in FIG. 1 in an initial position.

In the illustrated exemplifying embodiment, base frame 26 has a sensor unit 50, magazine 18 has a sensor unit 52, pickup unit 30 has a sensor unit 54, linear stroke element 44 has a sensor unit 56, angle element 48 has a sensor unit 58, and transport arm 46 has a sensor unit 60. Sensor units 50 to 60, each constituting microelectromechanical systems for sensing the rotation of the respective component to which they are connected, are each movable about two axes of a three-dimensional coordinate system that is independent of the position of the components, preferably about the axes of the coordinate system that lie in one horizontal plane. Angular deviations between two subassemblies respectively connected to a sensor 50 to 60 can thereby be ascertained. If this ascertained angular offset deviates from a target offset, an information item regarding that deviation can be outputted via a suitable display unit. Alternatively or additionally, it is possible to calculate a correction value that can be taken into account in the application of control to a drive unit for positioning the respective subassembly. Said correction value can be used in particular as an offset value in order to define a target position for positioning by the drive unit. The sensor units can be configured to sense rotations in three axes. This can be accomplished using two sensor modules in each sensor for respectively sensing rotations about two of the axes, as shown, for example by modules 50' and 50" corresponding to sensor 50 and modules 56' and 56" corresponding to sensor 56.

As a function of the angular deviations ascertained with the aid of sensor units 50, 52 between magazine 18 and base frame 26, adjusting screws 20 to 24 can be used for position correction, i.e. for alignment, by modifying the relative position of magazine 18 with respect to base frame 26 with the aid of said adjusting screws 20 to 24.

Magazine 18 is arranged at an inclination with respect to a horizontal plane, so that side wall 18a of magazine 18 forms a lateral stop for stack 14, so that the position of upper coverslip 16 upon removal thereof with the aid of pickup unit 30 has a desired defined position.

Figure 2:
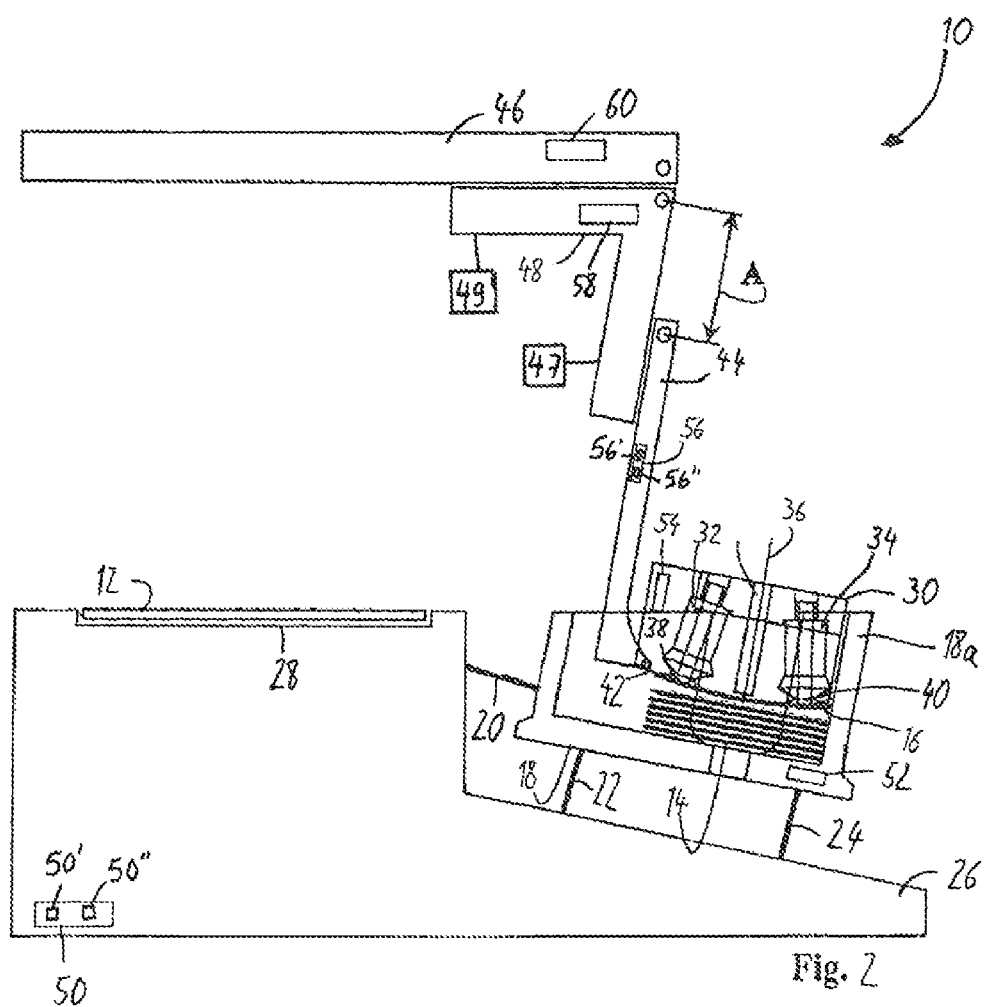
FIG. 2 is a side view of the arrangement according to FIG. 1 in a first operating position.

Apparatus 10 according to FIG. 1 is depicted in FIG. 2 in an operating position. Elements having the same configuration or the same function have the same reference characters. Linear stroke element 44 has been shifted downward over a distance A by a drive unit 47 on angle element 48 controlled by control unit 49, so that suction elements 38, 40 of pickup elements 32, 34 have contacted upper coverslip 16, upper coverslip 16 adhering to suction elements 38, 40 as a result of a negative pressure applied to pickup elements 32, 34. The drive unit 47 may be a stepping motor or linear motor. As a result of the displacement of pickup elements 32, 34 along their longitudinal axis, the picked-up coverslip 16 rests against end face 42 of pickup unit 30, so that coverslip 16 is curved both because of the arrangement of pickup elements 32, 34 and because of the shape of end face 42.

Figure 3:
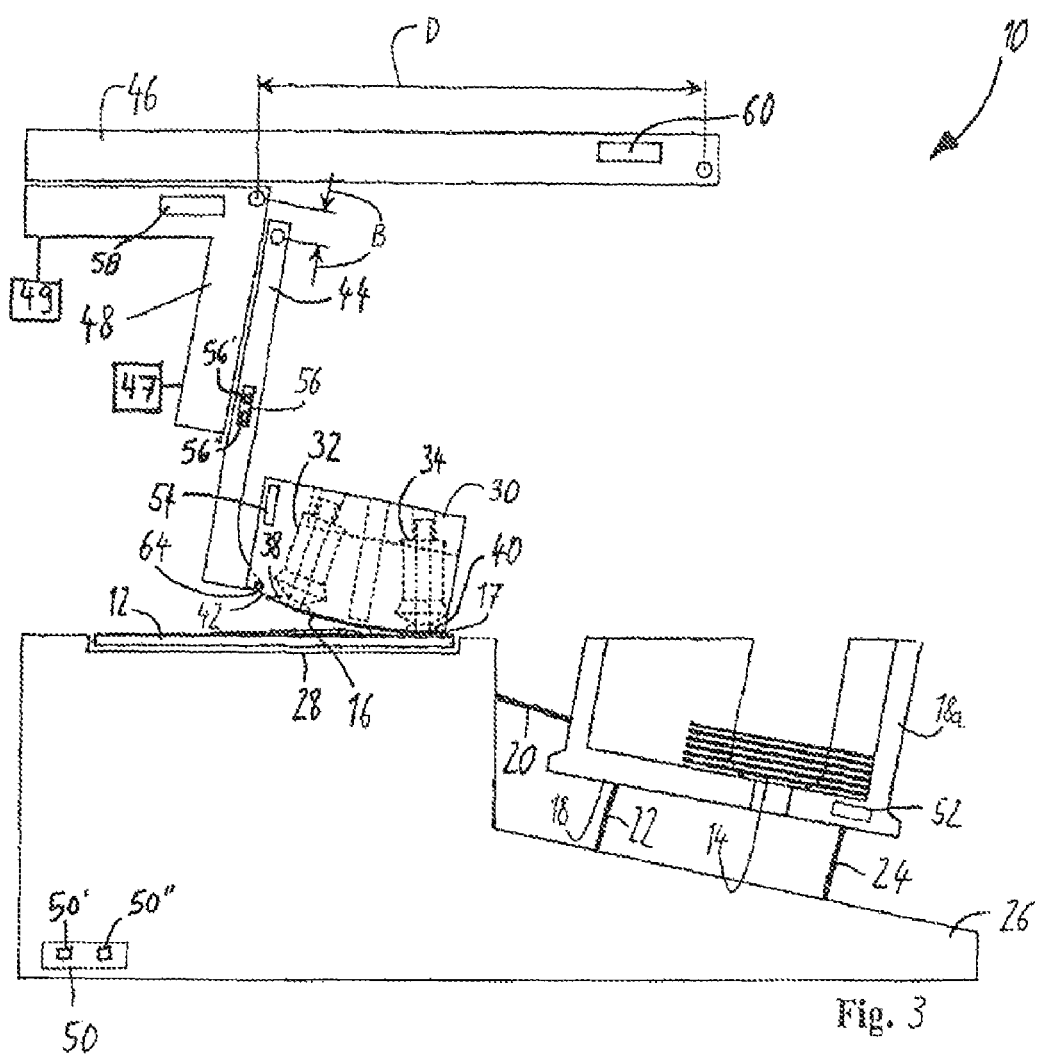
FIG. 3 is a side view of the arrangement according to FIGS. 1 and 2 in a second operating position.
Figure 4:
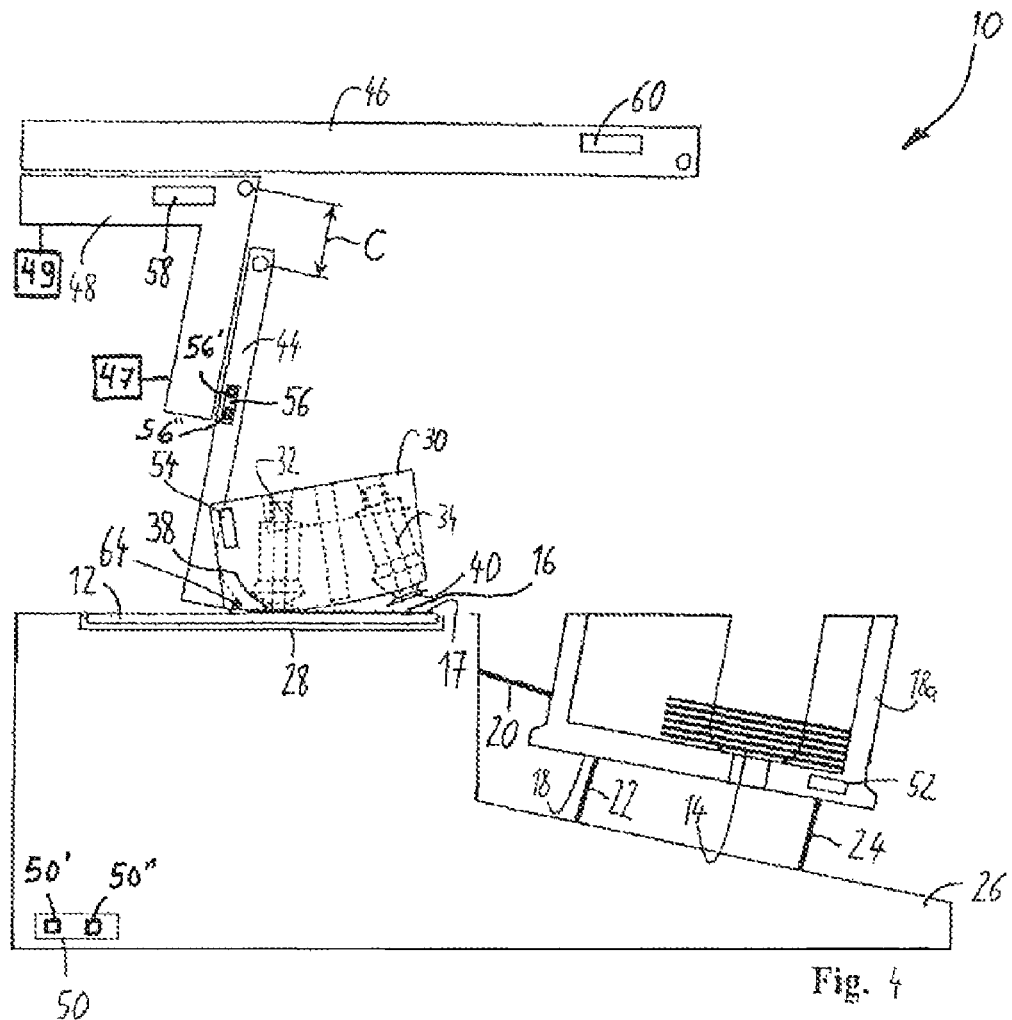
FIG. 4 is a side view of the arrangement according to FIGS. 1 to 3 in a third operating position.

Apparatus 10 according to FIGS. 1 and 2 is shown in FIG. 3 in a second operating position. As compared with the first working position shown in FIG. 2, linear stroke element 44 has been shifted back into the position shown in FIG. 1. Angle element 48 has then been moved over a distance D along transport arm 46, so that pickup unit 30 having coverslip 16 is arranged above specimen slide 12. Once coverslip 16 has been brought into a correct position above specimen slide 12, linear stroke element 44 is moved downward over a distance B, so that initial contact between coverslip 16 and the surface of specimen slide 12 to be covered is made in a region close to a side edge 17 of coverslip 16. With the aid of an application unit, a coverslipping agent, for example a transparent adhesive, has previously been applied onto a sample applied on the side of specimen slide 12 facing away from base frame 26, which agent then serves for secure retention of coverslip 16 on specimen slide 12 and surrounds the sample present on specimen slide 12. Further lowering of linear stroke element 44 causes end face 42 of pickup unit 30, together with coverslip 16, to be in rolling contact on the surface of specimen slide 12, such that pickup unit 30 rotates about a rotation axis 64 in the context of a movement of linear stroke element 44 from linear distance B according to FIG. 3 to linear distance C according to FIG. 4. A suitable stop prevents pickup unit 30 from being pivoted away from linear stroke element 44 farther than the position depicted in FIGS. 1 to 3. In the context of the movement of linear stroke element 44 from distance B to distance C, the negative pressure applied to pickup element 34 is equalized, or alternatively a positive pressure is applied, so that coverslip 16 detaches from suction element 40 and the specimen slip remains behind on specimen slide 12.

Figure 5:
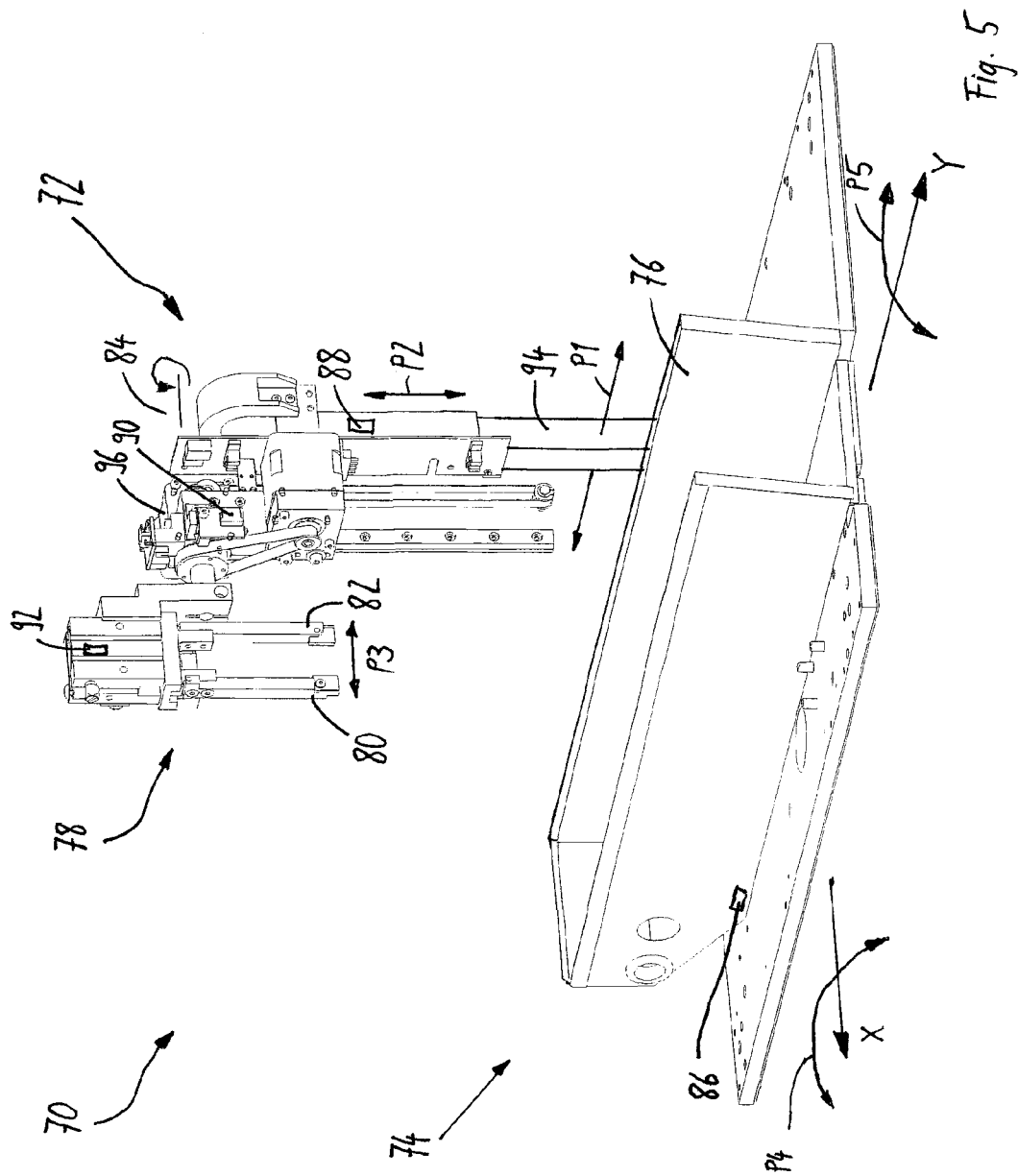
FIG. 5 is a perspective view of an arrangement of a base module and an actuation arm of a device for manipulating specimen slides, in accordance with another embodiment of the invention.

FIG. 5 shows components 72, 74 of an apparatus 70 for manipulating specimen slides, in accordance with another embodiment of the invention. Component 74 of apparatus 70 is a base frame having a cassette receiving unit 76, connected to base frame 74, for cassettes having multiple specimen slides inserted into receiving regions of the cassettes, which slides are individually removed from the cassette with the aid of apparatus 70 for further manipulation. Component 72 is an actuation element having elements movable in the direction of double arrows P1 to P3. A grip element 78 of actuation apparatus 72 can be positioned for the removal of specimen slides that are contained in one of the cassettes arranged in cassette receiving unit 76.

The specimen slides are arranged vertically on one side edge in the cassette, grip element 78 being positioned, for removal of the specimen slides, in such a way that it grips, with the aid of pressure elements 80, 82, on the sides adjoining the side on which the specimen slide stands in the cassette, and pulls the respective specimen slide upward out of the cassette. By means of a further displacement movement of actuation unit 72, and a rotation of grip element through 90° about rotation axis 84, the specimen slide is brought from a vertical position into a horizontal position in which a coverslipping agent and a coverslip are then applied onto a sample arranged on the upper side of the specimen slide.

Provided for this purpose is a further actuation arm that contacts the specimen slide, positioned horizontally with the aid of grip element 78, on the underside and supports it from below during further manipulation so that the specimen slide has a constant position especially when a coverslip is pressed onto the specimen slide. Thanks to correct positioning of the actuation arms, neither the specimen slide nor the coverslip is damaged or destroyed. The contact pressure support made available via a further actuation element must be exactly positioned with respect to grip element 78 and to the specimen slide clamped in grip element 78. Provided for this purpose, according to the present invention, are at least two sensor elements that ascertain the rotation of individual components 72, 74 and of further constituents or parts of components 72, 74. This is accomplished, in particular, by the fact that rotation about an axis of a coordinate system is ascertained. In the present exemplifying embodiment, a sensor unit 86 is arranged on base frame 74 of apparatus 70, a sensor unit 88 is arranged on a support 94 that is movable in the direction of arrow P1, a sensor unit 90 is arranged on a positioning unit 96 that is movable in the direction of arrow P2, and a sensor unit 92 is arranged on the pivotable grip element 78. As a result, the positions of elements of actuation unit 72 with respect to one another and to base frame 74, or to the cassette having specimen slides that is arranged in cassette receiving unit 76 of base frame 74, can be determined, and can be taken into account in the displacement movements of elements 74, 94, 96, 78 in order to arrange said elements 74, 94, 96, 78 exactly in three dimensions at a target position and/or to arrange the elements, as well as further elements, in a target position with respect to one another. Laborious alignment actions for exact alignment of the components with respect to one another are thus no longer necessary, or the alignment actions can be assisted by way of the sensor signals outputted from sensor units 86 to 92. In the present exemplifying embodiment, sensor unit 86 of base frame 74 ascertains a rotation about the X axis and a rotation about the Y axis of a coordinate system, the rotation being indicated with the aid of arrows P4 and P5. The further sensor units 88 to 92 also sense the rotation of the respective components about the X axis and the Y axis, so that in simple fashion, the position and orientation of the individual subassemblies with reference to their rotation about the X axis and the Y axis can be ascertained and compared with one another. In the event of deviations from a target position relative to another component or to the coordinate system, correction values can be ascertained that can then be taken into account in the context of positioning with the aid of drive units or, alternatively, can be used for correct alignment of the subassemblies with respect to one another with the aid of suitable alignment means.

Figure 6:
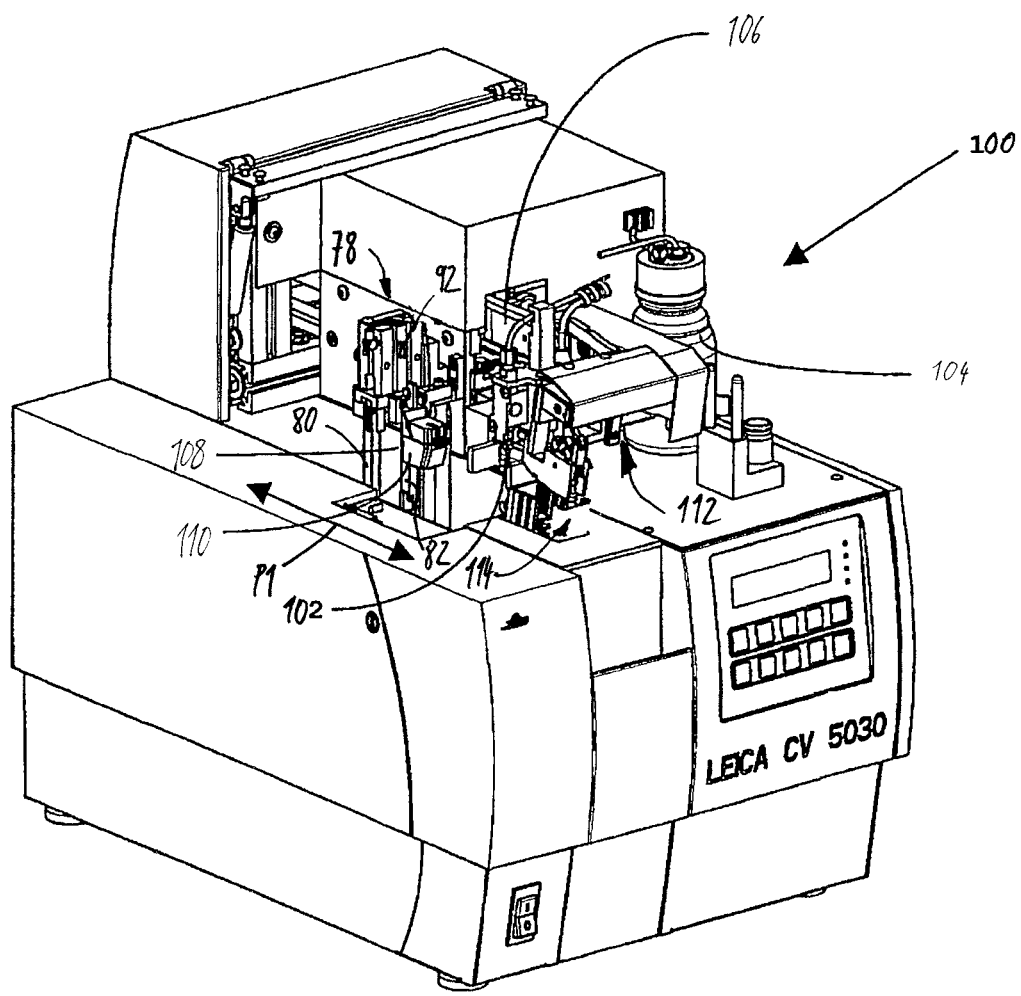
FIG. 6 is a three-dimensional schematic view of a coverslipping machine having an arrangement according to FIG. 5, in accordance with another embodiment of the invention.

FIG. 6 is an external view of a coverslipping machine 100 having an arrangement 70 according to FIG. 5. The coverslipping machine has a hollow needle 102 that applies a coverslipping agent from a supply container 104 onto a specimen slide. Hollow needle 102 is arranged on a guide 106 and is movable along said guide 106 in the double-arrow direction. Coverslipping machine 100 further encompasses a cleaning device 108 that has a container 110 having a cleaning liquid. Coverslipping machine 100 encompasses the components of apparatus 70 that are depicted in FIG. 5, individual elements being concealed by the housing of coverslipping machine 100. Grip element 78 having pressure elements 80, 82, as well as sensor unit 92 connected to grip element 78, are shown in a working region. Coverslipping machine 100 further encompasses a subassembly 112 for manipulating the coverslips and a subassembly 114 for supporting a specimen slide upon application of the coverslip. These two subassemblies each encompass further sensor units arranged on relevant constituents, with each of which units it is possible to ascertain the positions of the constituents with respect to further constituents of coverslipping machine 100 that require correct mutual orientation.

With use of the invention, passive orientation aids such as spirit levels, automatic leveling devices, in particular motor-driven support feet for base plates of housing, and similar orientation means in order to orient individual components in three dimensions are not necessary. The invention makes possible, in simple fashion, exact automatic orientation of movable assemblies with respect to one another, regardless of perpendiculars, in order to avoid misalignments. The setup effort upon initial commissioning of apparatuses for manipulating specimen slides can thereby be considerably reduced. Thanks to the device, the base plate or base module of a device no longer needs to be oriented exactly in a horizontal plane, since movable assemblies must have a defined angle relative to the base modules at least in a working position that is ascertained given a knowledge of the positional deviation of base frame 74 based on a knowledge of the rotation of base frame 74 about at least one axis of the coordinate system, and is taken into account in the positioning of the movable assemblies relative to base frame 74. Laborious manual alignment of the individual components and assemblies is therefore not necessary. In addition, manufacturing tolerances can also be compensated for in this fashion. The positions of individual components are determined with the aid of the sensor units and, based on geometrical laws, correction values are calculated for orientation of the components in three dimensions or for correct positioning of the components with respect to one another. With the aid of the position ascertained by means of sensor unit 86 of base frame 74 it is possible, on the basis of a desired target position of a movable assembly relative to base frame 74, to identify as a target value a value to be outputted by sensor unit 92 of a movable subassembly 78 in the correct position, and to move subassembly 78, with the aid of a drive unit, until sensor 92 of subassembly 78 outputs that value.

All the sensor units of the exemplifying embodiments may include at least one microelectromechanical system (MEMS). A microelectromechanical system of this kind preferably encompasses a gyroscope and/or an acceleration sensor. Inclinometers, for example, may be utilized.

While the invention has been particularly shown and described with reference to preferred embodiments thereof, it will be understood by those skilled in the art that various changes in form and details may be made therein without departing from the spirit and scope of the invention.

PARTS LIST 10, 70 Apparatus
12 Specimen slide
14 Stack
16 Coverslip
17 Side of coverslip
18 Magazine
18a Side wall of magazine
20 to 24 Adjusting screw
26 Base frame
28 Specimen slide receiving region
30 Pickup unit
32, 34 Pickup element
36 Center axis
38, 40 Suction elements
42 End face
44 Linear stroke element
46 Transport arm
48 Angle element
50 to 60 Sensor element
64 Rotation axis
72, 74 Component
76 Cassette receiving unit
78 Grip element
80, 82 Pressure element
84 Rotation axis
86 to 92 Sensor unit
94 Displaceable support
96 Displaceable positioning unit
100 Coverslipping machine
102 Hollow needle
104 Supply container
106 Guide
108 Cleaning unit
110 Container
112, 114 Subassemblies
P1 to P5 Motion direction arrows
A to D Positioning distances

We claim:

1. A device for manipulating at least one specimen slide, the device comprising:
   a first sensor unit operable to sense a first rotation of a first component of the device about at least one first axis of a three-dimensional coordinate system;
   a second sensor unit operable to sense a second rotation of a second component of the device about the at least one first axis of the coordinate system, the coordinate system being independent of a position of the first component and of a position of the second component; and
   a positioning unit operable to position the second component relative to the first component,
   wherein the first component includes a base module of the device, the base module configured to receive at least one of a specimen slide and a cassette including a plurality of specimen slides, such that the received specimen slide or plurality of specimen slides is held in a defined position relative to the base module;
   wherein the second component includes an actuation element movable relative to the base module by a drive unit,
   wherein the first and second sensor units each include at least one microelectromechanical system, and
   wherein at least one of the microelectromechanical systems include at least one of a gyroscope and an acceleration sensor.

2. The device as recited in claim 1, wherein the positioning unit includes at least one drive unit and at least one control unit, the control unit operable to control the drive unit so as to position the second component as a function of the first rotation of the first component sensed by the first sensor unit about the at least one first axis and as a function of the second rotation of the second component sensed by the second sensor unit about the at least one second axis such that the first component has at least one of a selectable first target position and selectable second target position relative to the second component at least with respect to a rotation of the first component about the at least one first axis.

3. The device as recited in claim 2, wherein the at least one drive unit includes at least one of a stepping motor and a linear motor.

4. The device as recited in claim 1, further comprising a third sensor unit operable to sense a rotation of a second actuation element about the at least one first axis of the coordinate system, the second actuation element being movable relative to the base module.

5. The device as recited in claim 1, wherein the first rotation is indicatable by an angle between a reference axis of the first component and a second axis of the coordinate system, and wherein the second rotation is indicatable by an angle between a reference axis of the second component and the second axis of the coordinate system.

6. The device as recited in claim 5, wherein the angle between the second axis of the coordinate system and the reference axis of the respective component is projectable on a plane orthogonal to the first axis of the coordinate system and defined by a second and third axis of the coordinate system.

7. The device as recited in claim 1, further comprising at least one of an automatic application unit operable to apply a biological sample onto a specimen slide, an automatic cleaning unit operable to remove substances surrounding the biological sample, an automatic staining unit operable to stain a biological sample disposed on the specimen slide, and an automatic coverslipping unit operable to cover the biological sample disposed on the specimen slide with at least one of a coverslipping agent and a coverslip.

* * * * *